(12) United States Patent
Ek et al.

(10) Patent No.: US 12,207,852 B2
(45) Date of Patent: *Jan. 28, 2025

(54) SYSTEM AND METHOD FOR BONE FIXATION

(71) Applicant: Arthrosurface Incorporated, Franklin, MA (US)

(72) Inventors: Steven W. Ek, Durham, NH (US); George Sikora, Bridgewater, MA (US); S. Brent Brotzman, Austin, TX (US)

(73) Assignee: Arthrosurface Incorporated, Franklin, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/327,656

(22) Filed: Jun. 1, 2023

(65) Prior Publication Data

US 2023/0371992 A1 Nov. 23, 2023

Related U.S. Application Data

(63) Continuation of application No. 16/878,017, filed on May 19, 2020, now Pat. No. 11,712,276, which is a continuation of application No. 13/723,902, filed on Dec. 21, 2012, now abandoned.

(60) Provisional application No. 61/579,318, filed on Dec. 22, 2011.

(51) Int. Cl.
*A61B 17/84* (2006.01)
*A61B 17/86* (2006.01)
*A61B 17/72* (2006.01)

(52) U.S. Cl.
CPC ......... *A61B 17/84* (2013.01); *A61B 17/8685* (2013.01); *A61B 17/7291* (2013.01)

(58) Field of Classification Search
CPC .. A61B 17/7291; A61B 17/84; A61B 17/8685
See application file for complete search history.

(56) References Cited

U.S. PATENT DOCUMENTS

2006/0167559 A1* 7/2006 Johnstone ............. A61F 2/4261
623/23.46

* cited by examiner

*Primary Examiner* — Samuel S Hanna
(74) *Attorney, Agent, or Firm* — Grossman, Tucker, Perreault & Pfleger, PLLC

(57) ABSTRACT

A fixation system for coupling a first and a second portion of bone together. The fixation system includes a first fixation element, a second fixation element, and an interconnect. The first fixation element includes an external surface configured to engage the first portion of bone and a first tapered mating surface. The second fixation element includes an external surface configured to engage the second portion of bone and a second tapered mating surface. The interconnect includes a first and a second tapered surface disposed at generally opposite ends. The first and the second tapered surfaces are configured to frictionally engage the first and the second tapered mating surfaces of the first and the second element, respectively, to form frictional interference connections therebetween.

17 Claims, 16 Drawing Sheets

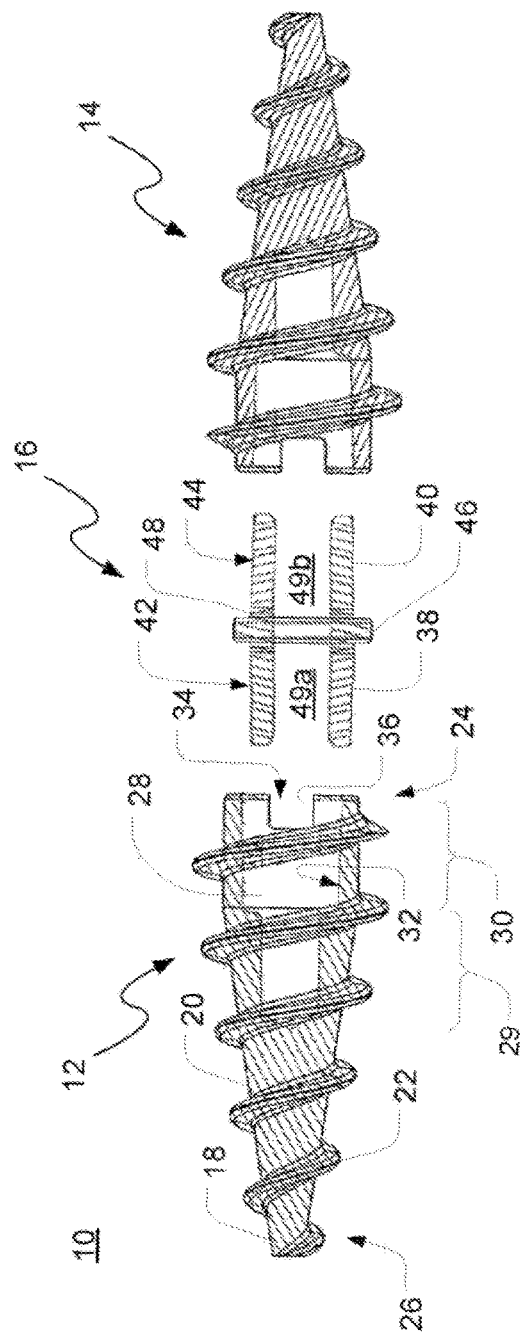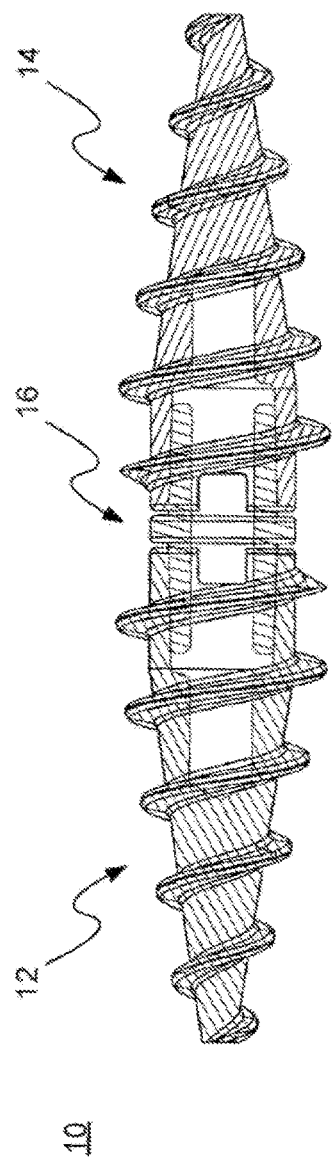
FIG. 1
FIG. 2

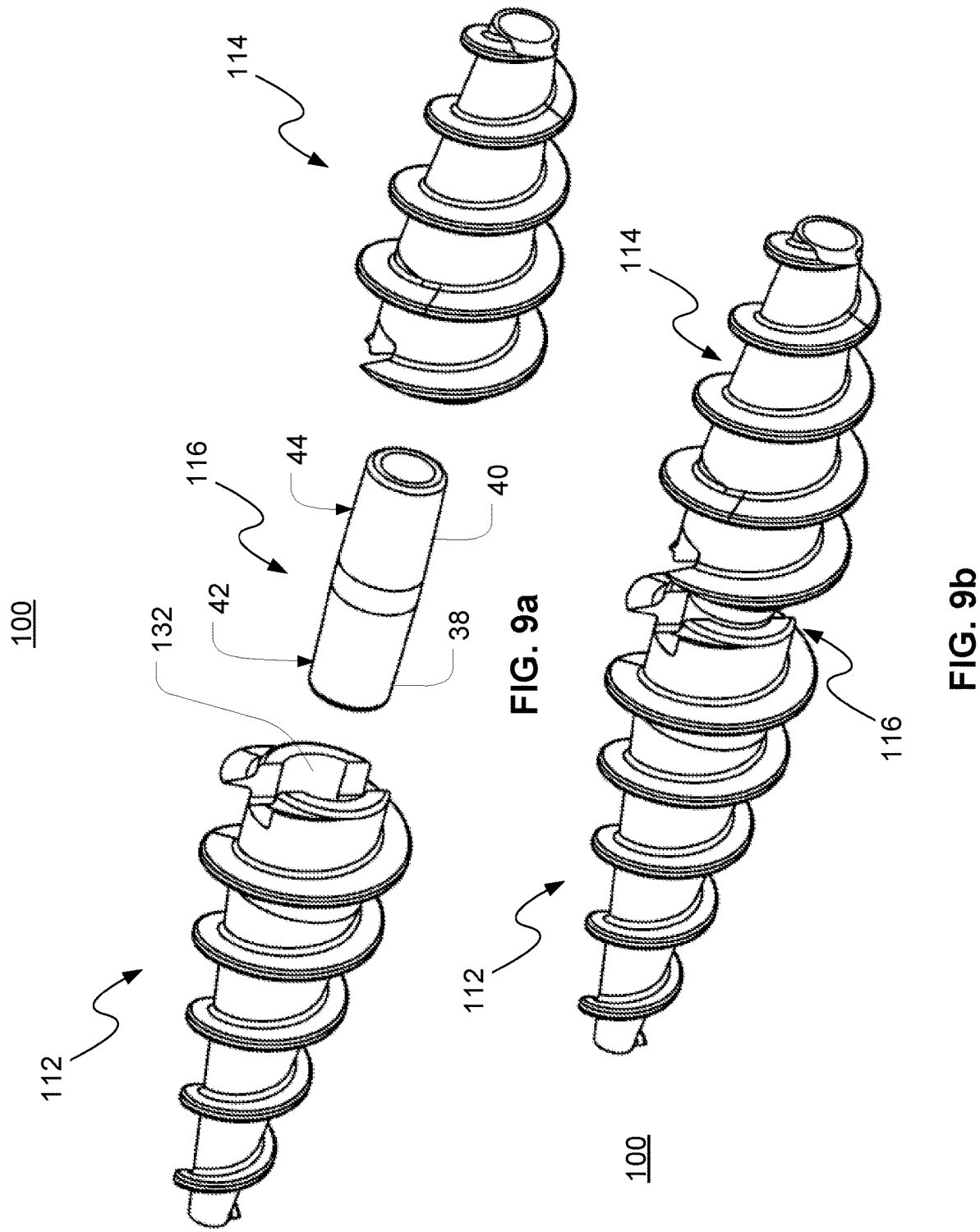

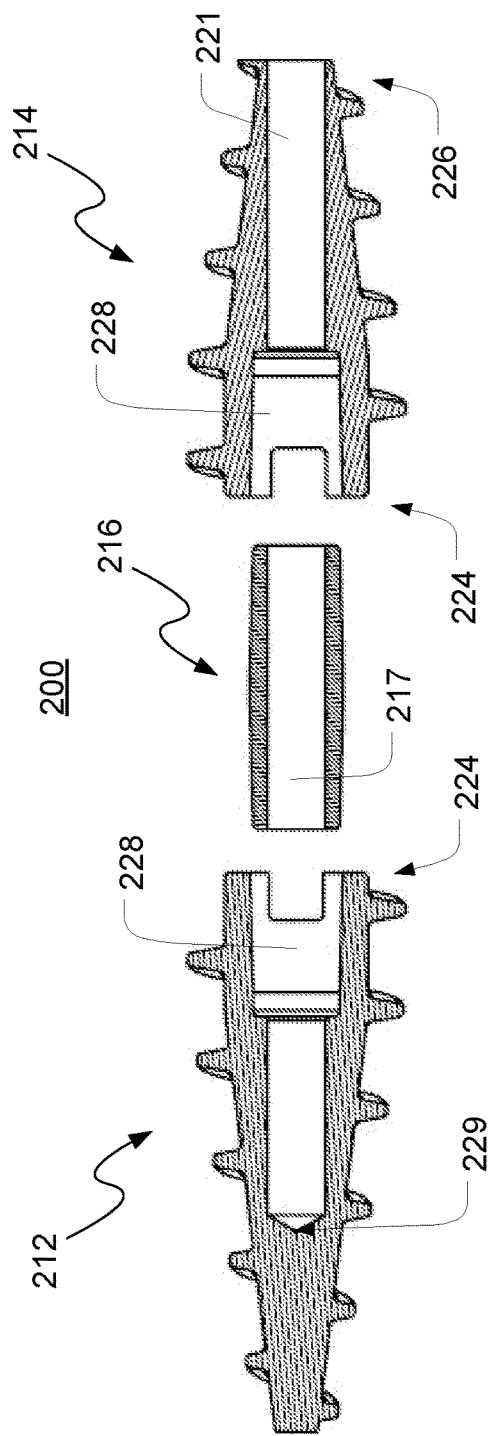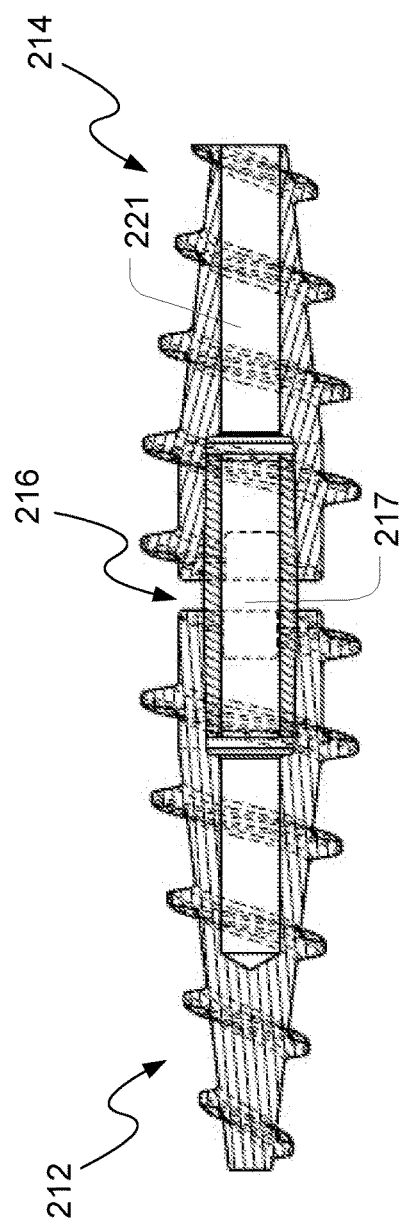
FIG. 10a
FIG. 10b

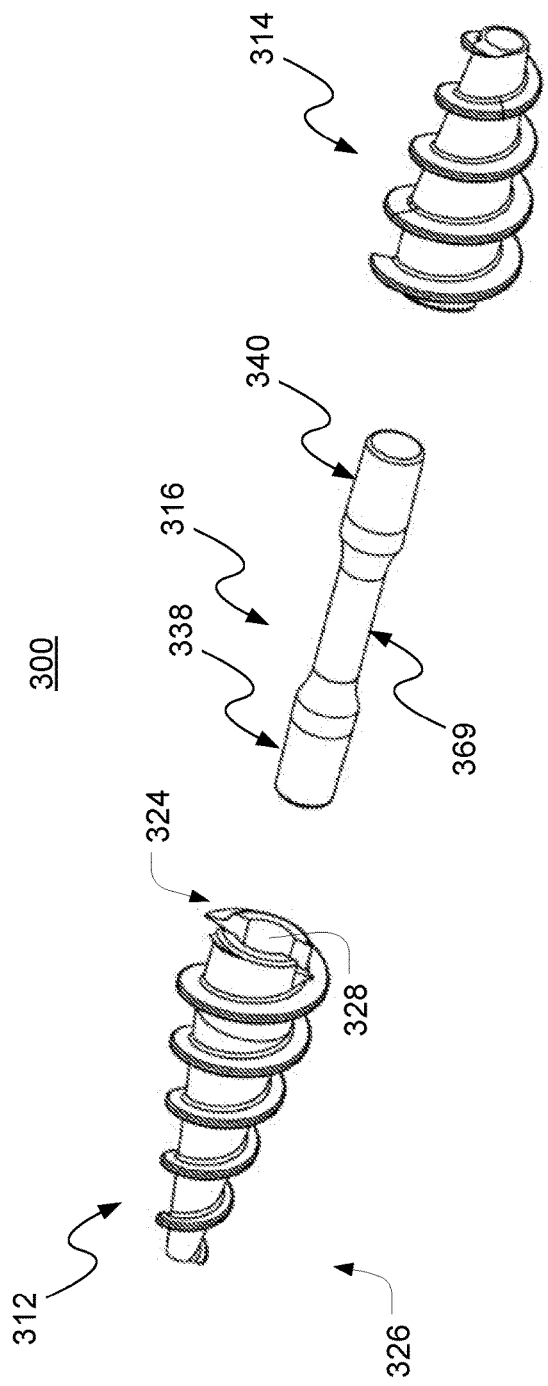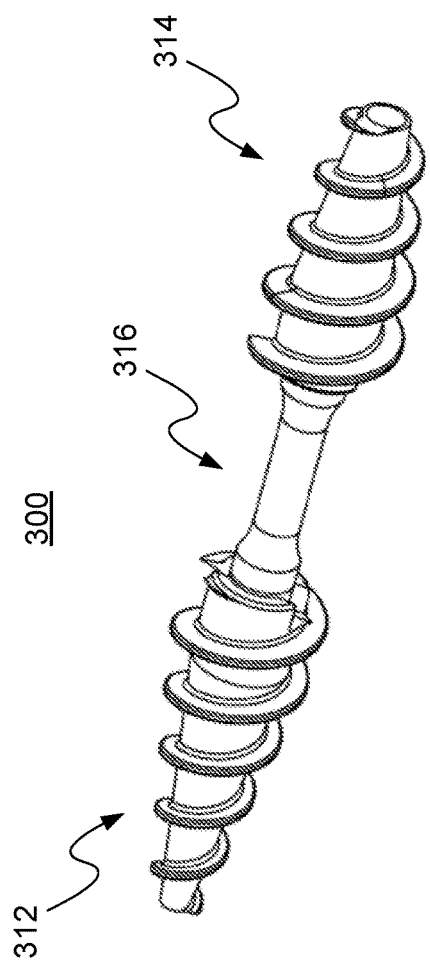
FIG. 11a
FIG. 11b

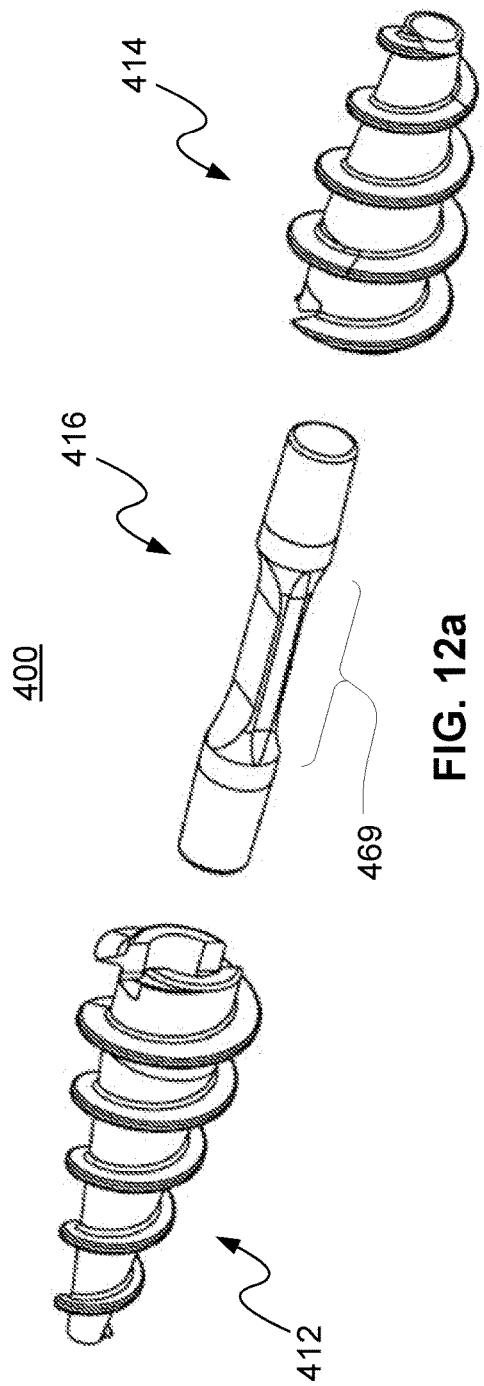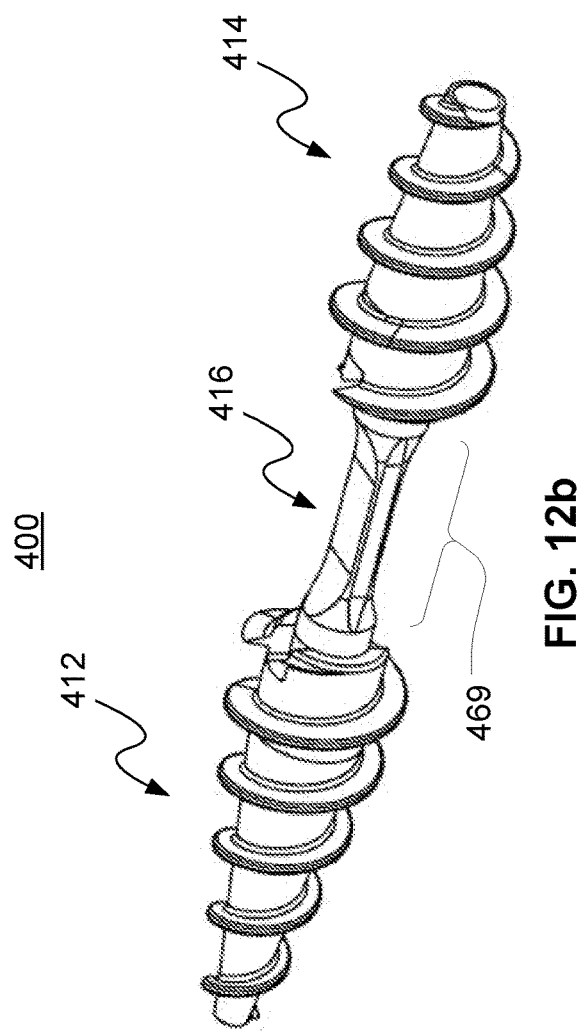

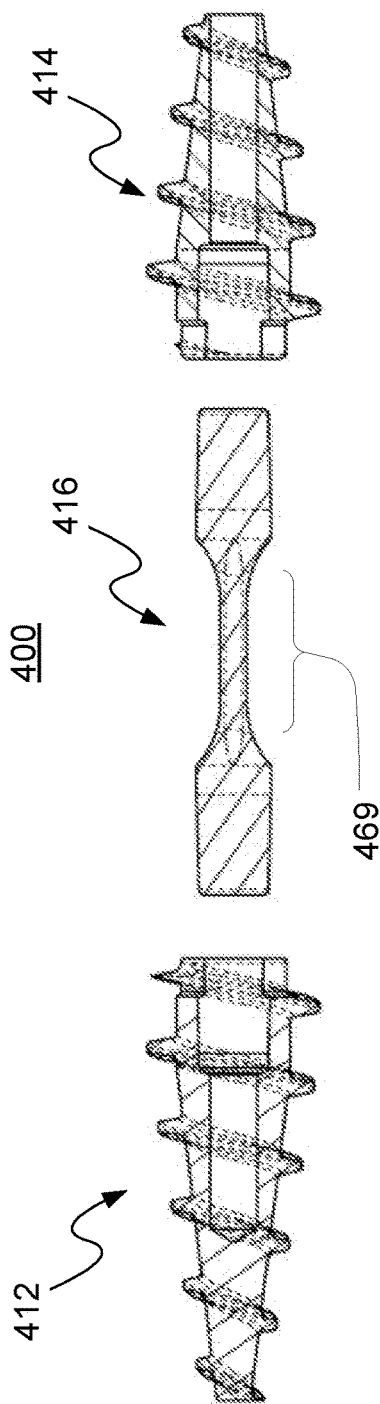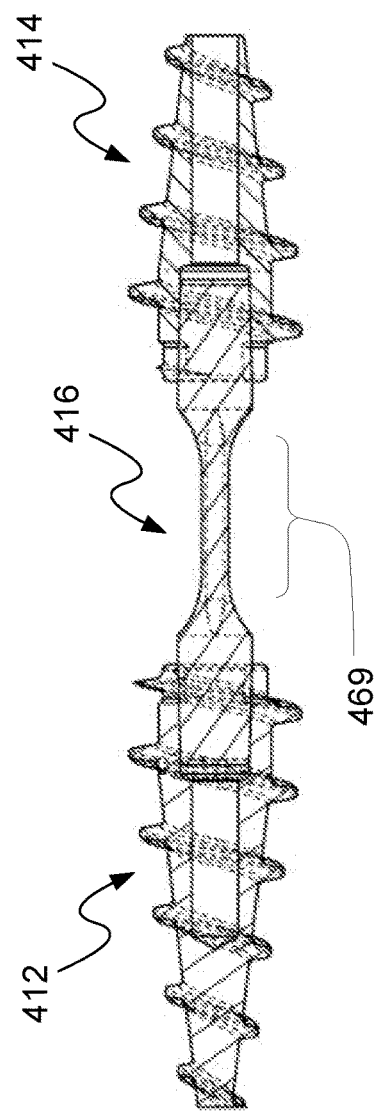
FIG. 12c
FIG. 12d

SYSTEM AND METHOD FOR BONE FIXATION

CROSS REFERENCE TO RELATED APPLICATIONS

This application is a continuation U.S. patent application Ser. No. 16/878,017, filed May 19, 2020, which is a continuation of U.S. patent application Ser. No. 13/723,902, filed Dec. 21, 2012, which is fully incorporated herein by reference. This application also claims the benefit of U.S. Provisional Application Ser. No. 61/579,318, filed Dec. 22, 2011, which is fully incorporated herein by reference.

FIELD

This disclosure relates to biological medical devices and methods, and particularly to biological medical implants and methods for bone fixation.

BACKGROUND

In many circumstances, it may be desirable to couple two or more bone segments together. For example, a single bone may be damaged in two or more portions and/or two or more adjacent bones may be out of alignment with respect to each other. The joint between two bones may have wear or other problems. In either situation, it may be beneficial to couple and/or secure the bones/bone segments together such that the bones/bone segments are generally anatomically aligned with respect to each other.

BRIEF DESCRIPTION OF THE DRAWINGS

Features and advantages of the present invention are set forth by description of embodiments consistent with the present invention, which description should be considered in conjunction with the accompanying drawings wherein:

FIG. 1 is a cross-sectional view exploded view of a fixation system consistent with one embodiment of the present disclosure;

FIG. 2 is a cross-sectional view of the assembled fixation system of FIG. 1;

FIGS. 9a-9b illustrate various views of a fixation system consistent with another embodiment of the present disclosure;

FIGS. 10a-10b illustrate various views of a fixation system consistent with yet another embodiment of the present disclosure;

FIGS. 11a-11d illustrate various views of a fixation system consistent with yet a further embodiment of the present disclosure;

FIGS. 12a-12d illustrate various view of a fixation system consistent with yet a further embodiment of the present disclosure;

DETAILED DESCRIPTION

Figure 3:
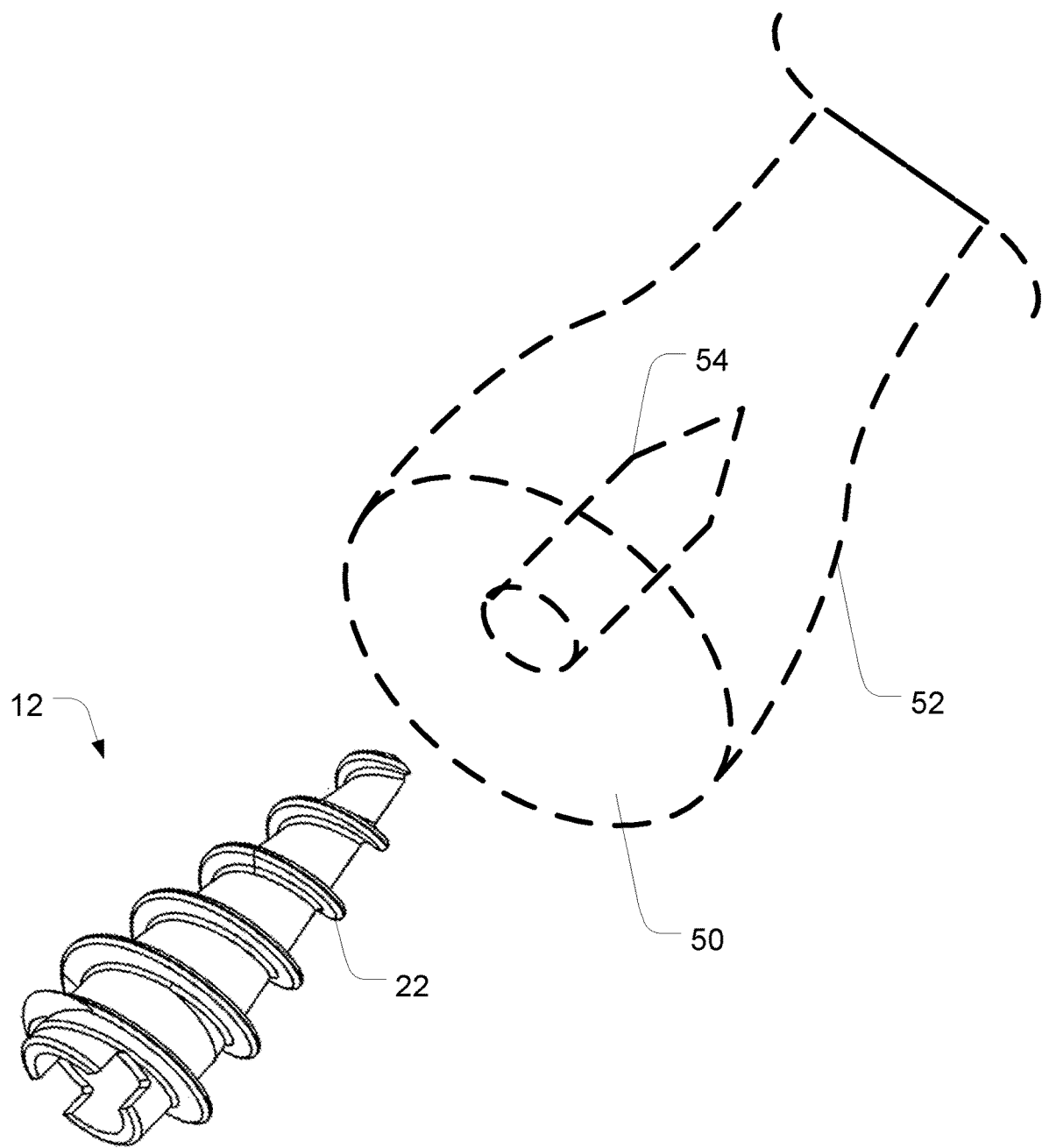
FIGS. 3-8 illustrate various steps of securing two bones together using a fixation system consistent with the present disclosure.

By way of summary, one embodiment of the present disclosure may feature a fixation system and method for coupling together two bone or bone segments. The fixation system may include a first and a second fixation element (e.g., but not limited to, a screw) and an interconnect. The first and second fixation elements are coupled to a first and second bone, respectively, and each includes a tapered cavity. The interconnect includes a first and a second tapered protrusion configured to be frictionally received in the tapered cavities of the first and second fixation elements, respectively. Once assembled, the frictional forces between the tapered surfaces form a frictional connection which generally locks the position of the first and second fixation elements together with respect to each other (though the fixation system may also be configured to allow some movements relative to each other).

Turning now to FIGS. 1 and 2, one embodiment of a fixation system 10 is generally illustrated in an unassembled (i.e., exploded) cross-sectional view (see FIG. 1) and an assembled cross-sectional view (see FIG. 2). The fixation system 10 includes a first and a second fixation element 12, 14 as well as an interconnect 16. As described herein, the fixation system 10 may be used to couple and/or secure to bones and/or bone segments (collectively generally referred to as simply bones for ease of reference) together with respect to each other. The fixation system 10 may therefore be used to arrange or position the bones in a generally anatomically alignment. As used herein, the term "generally anatomically alignment" is intended to mean a positioning of the bones corresponding to the generally accepted medical definition. The term "generally anatomically alignment" may therefore allow for some deviation based on the patient's overall condition, the skill of the surgeon, and pathology being treated.

In the illustrated embodiment, the first fixation element 12 is configured as a screw 18. According to one embodiment, the screw 18 includes a body portion 20 having one or more external threaded portions 22 configured to threadably engage with a portion of a first bone. The threaded portion 22 may include a self-taping thread. While the first fixation element 12 is shown having an external threaded portion 22, the body 20 of the first fixation element 12 may alternatively (or in addition) include one or more ribs or protrusions configured to engage the bone to secure the first fixation element 12 to the bone. A portion of the body 20 may have a tapered configuration which decreases from a first end 24 (e.g., a proximal end) to a second end 26 (e.g., a distal end).

At least a portion of the body 20 (e.g., but not limited to, the proximal end 24) defines a first cavity 28. The first cavity 28 may include a generally cylindrical region 30 having a tapered inner surface/sidewall 32. The tapered sidewall 32 decreases in diameter from the opening 34 of the cavity 28 towards the distal end 26. As described herein, the opening 34 of the cavity 28 is configured to receive a corresponding tapered portion of the interconnect 16 to form a frictional interference connection/coupling as generally illustrated in FIG. 2.

The proximal end 24 may also include one or more notches 36. Consistent with the illustrated embodiment, the screw 18 may be rotatably driven, i.e., screwed, into the bone using a driver (not shown for clarity) configured to engage the notches 36 to rotate the screw 18. Alternatively (or in addition), the first cavity 28 may include a keyed region 38 configured to engage with a corresponding keyed region of the driver to rotate the first fixation element 12 into the bone.

The second fixation element 14 is configured to be secured to a second bone and may generally correspond to the first fixation element 12. For example, the second fixation element 14 may be the same as the first fixation element 12. Alternatively, the second fixation element 14 may have a different diameter, length, pitch, taper, length of cannulated passage, and/or the like. The dimensions of the first and second fixation elements 12, 14 will depend on the intended application and related size of the first and second fixation elements 12, 14 dimensions and condition of the first and second bones to be coupled together. For example, the dimensions of the first and second fixation elements 12, 14 may be generally about 5 mm in diameter at the proximal outer diameter, tapering down over the 12 mm length of the screw to a 2.5 mm diameter at the distal outer diameter. The interconnect 16 may be approximately 2 mm in diameter and may vary from 6 mm to 13 mm in overall length.

The interconnect 16 is configured to couple the first and second fixation elements 12, 14, and therefore the first and second bones. The interconnect 16 includes a first and a second generally cylindrical region 38, 40 each having a tapered external surface/sidewall 42, 44, respectively. The tapered sidewalls 42, 44 have a taper which generally corresponds to the tapered sidewalls 32 of the first and second fixation elements 12, 14, respectively, to form a frictional or interference fit. In particular, when the interconnect 16 is received within the first and second fixation elements 12, 14, the precision tapered sidewalls 32 of the first and second fixation elements 12, 14 abut against the precision tapered sidewalls 42, 44 of the interconnect 16 so closely that the friction between the sidewalls 32, 42, 44 mates the first and second fixation elements 12, 14 to the interconnect 16 as generally illustrated in FIG. 2.

The interconnect 16 may optionally include one or more shoulders, protrusions, or the like 46. The shoulder 46 extends radially outwardly from the body 48 of the interconnect 16. According to one embodiment, the shoulder 46 extends circumferentially around the entire perimeter of the body 48. Alternatively, the shoulder 46 may extend radially outwardly around a portion of the body 48. The shoulder 46 may separate the first and second sidewalls 42, 44 as generally illustrated FIG. 1 and may limit the distance which the interconnect 16 may be inserted into a cavity 28 of fixation elements 12, 14 as generally illustrated in FIG. 2.

The interconnect 16 may also optionally define one or more internal cavities 49a, 49b. As described herein, the internal cavities 49 may be configured to receive an alignment device to facilitate alignment of an adjacent fixation element (e.g., the second fixation element 14).

Turning now to FIGS. 3-8, one embodiment of a method for coupling a first and a second bone together using a fixation system 10 consistent with at least one embodiment of the present disclosure is generally illustrated. In particular, an end 50 of a first bone 52 may be prepared as generally illustrated in FIG. 3. For example, a portion of the end 50 of the bone 52 may be removed to provide additional space for the fixation system 10 and/or to align the bone 52 with respect to the adjacent bones. Optionally, a pilot hole or the like 54 may be formed in the end 50 of the bone 52. The pilot hole 54 may be formed using a drill and/or a guide wire (not shown). The pilot hole 54 in the bone 52 may be configured to receive a portion of the first fixation element 12. For example, the pilot hole 54 may be configured to receive the first fixation element 12 and may have a diameter smaller than the outside diameter of the threads 22 of the first fixation element 12 to allow the threads 22 of the first fixation element 12 to engage the bone 52.

Figure 4:
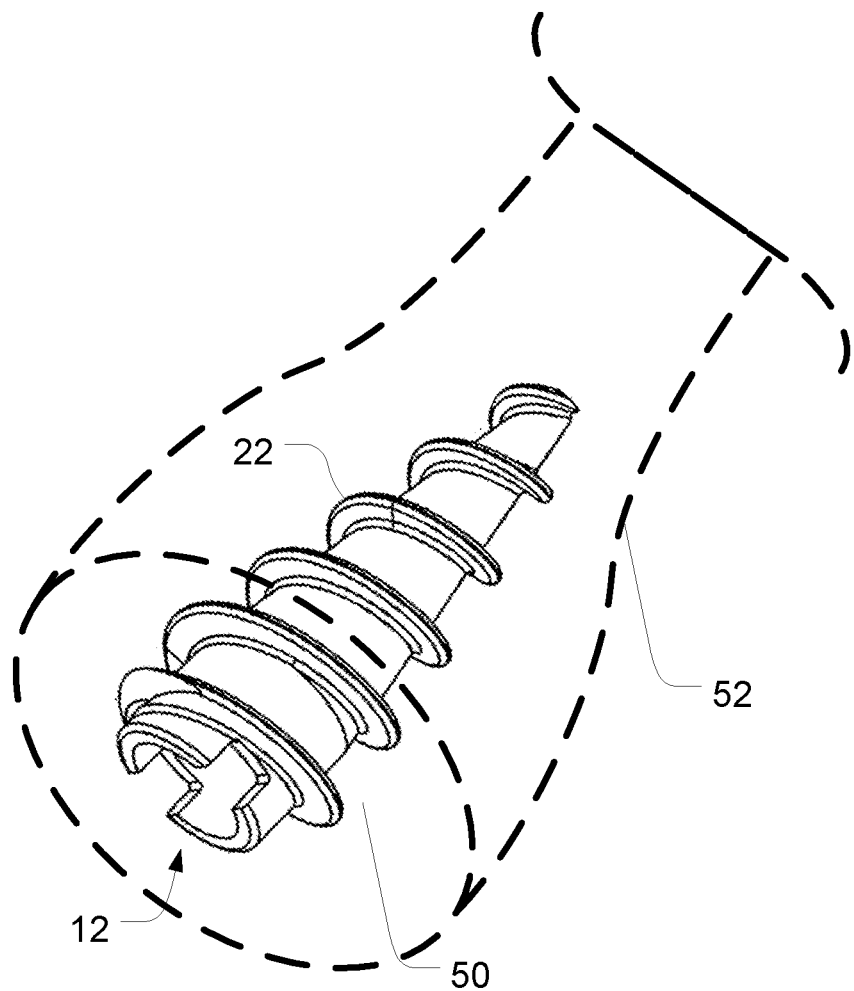

After the pilot hole 54 is formed, the first fixation element 12 may be rotatably driven (e.g., screwed) into the bone 52 (for example using a driver) as generally illustrated in FIG. 4. Again, it should be noted that the first fixation element 12 may be secured to the bone 52 without a pilot hole 54. The depth of the first fixation element 12 within the bone 52 may be set by rotating the first fixation element 12 until the first fixation element 12 is in the desired position. By adjusting the depth of the first fixation element 12 within the bone 52, the fixation system 10 may be used in a wider variety of applications. For example, adjusting the depth of the first fixation element 12 may compensate for different amounts of bone preparation (e.g., removal of bone at the end).

Figure 5:
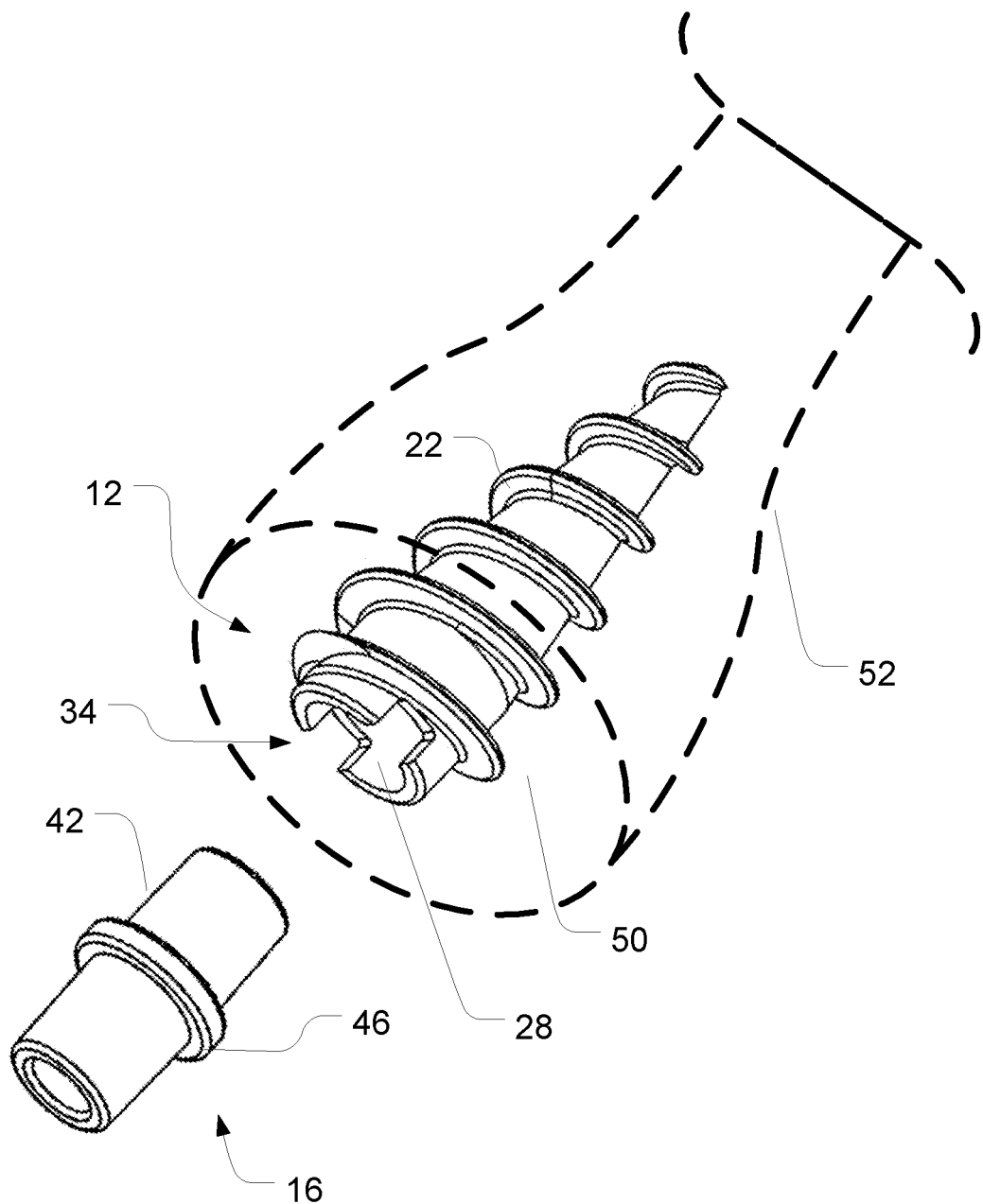
Figure 6:
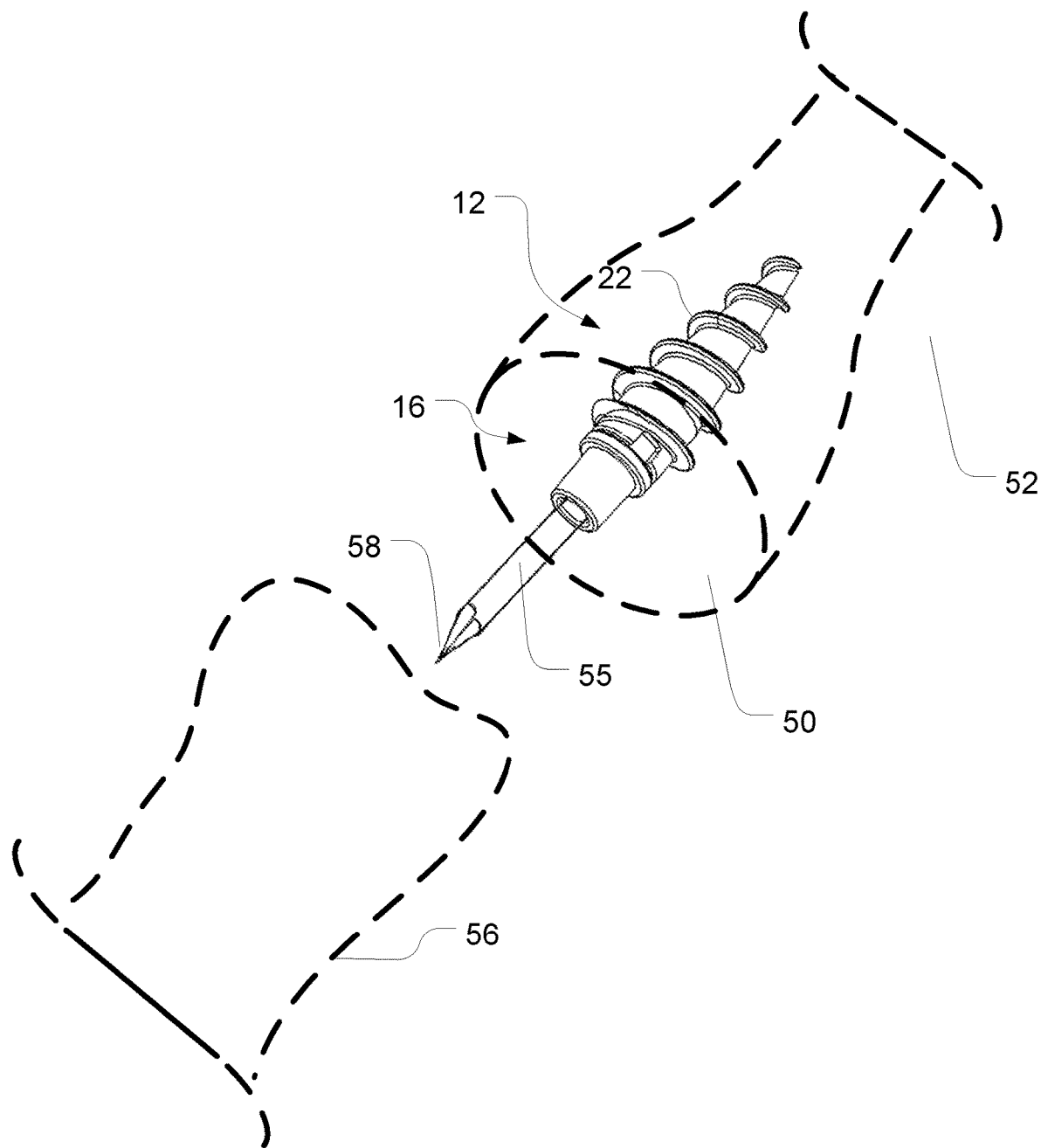

After the first fixation element 12 is secured in the first bone 52, a first tapered sidewall 42 of the interconnect 16 may be co-axially received in the opening 34 of the cavity 28 of the first fixation element 12, for example, as generally illustrated in FIGS. 5 and 6. As seen, the sidewall 42 of the interconnect 16 may be inserted into the cavity 28 of the first fixation element 12 until the shoulder 46 abuts against the proximal end 24 of the first fixation element 12. Optionally, an alignment device 55 may be used to locate where the second fixation element 14 should be secured to the second bone 56. For example, the alignment device 55 may include a pin configured to be received in the cavity 49 of the interconnect 16. The pin 55 may be secured within the cavity 49 and extend beyond the interconnect 16. The second bone 56 may then be placed into axial alignment with the pin 55. The pin 55 may include a pointed tip 58 which may pierce and/or mark the location on the second bone 56 where the second fixation element 14 should be secured.

Optionally, the pin 55 may be secured into the second bone 56, and a pilot hole may be formed in the second bone 56 using a cannulated drill bit advanced over the pin 55.

Figure 7:
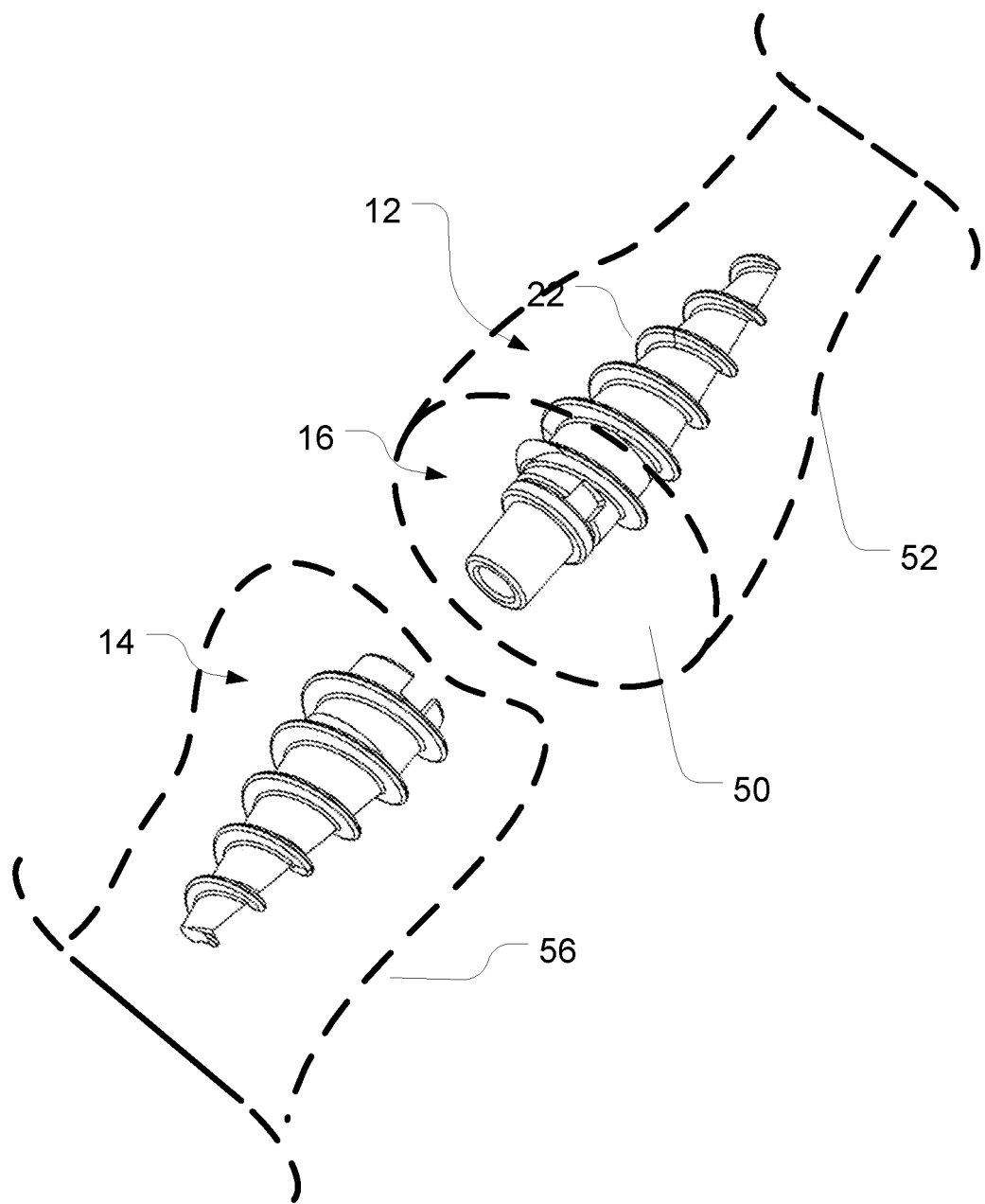

After the location of the second fixation element 14 has been determined, the second fixation element 14 may be rotatably driven (e.g., screwed) into the bone 56 (for example using a driver) as generally illustrated in FIG. 7. Again, it should be noted that the second fixation element 14 may be secured to the bone 56 without a pilot hole. The depth of the second fixation element 14 within the bone 56 may be set by rotating the second fixation element 14 until the second fixation element 14 is in the desired position. By adjusting the depth of the second fixation element 14 within the bone 56, the fixation system 10 may be used in a wider variety of applications. For example, adjusting the depth of the second fixation element 14 may compensate for different amounts of bone preparation (e.g., removal of bone 56 at the end).

Figure 8:
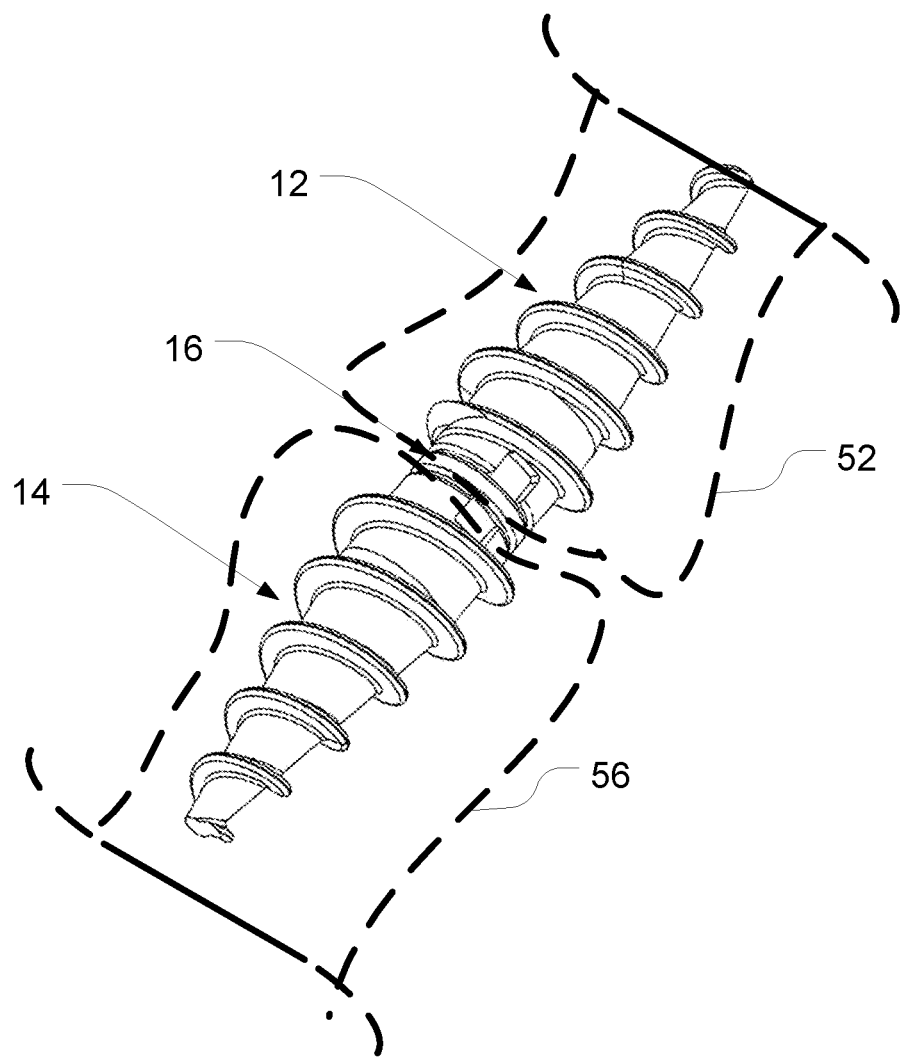

After the second fixation element 14 has been secured in the second bone 56, the second tapered sidewall 44 of the interconnect 16 may be co-axially received in the opening 34 of the cavity 28 of the second fixation element 14, for example, as generally illustrated in FIG. 8. As seen, the sidewall 44 of the interconnect 16 may be inserted into the cavity 28 of the second fixation element 14 until the shoulder 46 abuts against the proximal end 24 of the second fixation element 14.

It may be appreciated that the depth of first and second fixation elements 12, 14 may be set independent of each other and independent of the interconnect 16. More specifically, while the depth of the first and second fixation elements 12, 14 determines the separation distance between the first and second bones 52, 56, the first and second fixation elements 12, 14 and the interconnect 16 are not limited to a specific orientation relative to each other. As such, the separation distance between the first and second bones 52, 56 may be infinitely adjustable.

It should be appreciated that the various steps in the method described herein do not necessarily have to be performed in any specific order. For example, the first and the second fixation elements 12, 14 may be secured in the bones prior to the interconnect 16 being coupled with either of the fixation elements 12, 14.

Turning now to FIGS. 9a and 9b, an exploded view (FIG. 9a) and assembled view (FIG. 9b) of another embodiment of a fixation system 100 is generally illustrated. The fixation system 100 includes a first and a second fixation element 112, 114 as well as an interconnect 116. The first and second fixation elements 112, 114 may be similar to any fixation elements described herein. The interconnect 116 includes a first and a second generally cylindrical region 138, 140 each having a tapered external surface/sidewall 142, 144, respectively. The tapered sidewalls 142, 144 have a taper which generally corresponds to the tapered sidewalls 132 of the first and second fixation elements 112, 114, respectively, to form a frictional or interference fit as generally illustrated in FIG. 9b and as generally described herein. The interconnect 116 of FIGS. 9a and 9b does not have a shoulder.

With reference to FIGS. 10a and 10b, an exploded view (FIG. 10a) and assembled view (FIG. 10b) of yet another embodiment of a fixation system 200 is generally illustrated. The fixation system 200 includes a first and a second fixation element 212, 214 as well as an interconnect 216. While the interconnect 216 is illustrated without a shoulder, this is not a limitation of the present disclosure unless specifically claimed as such and the interconnect 216 may include any interconnect described herein. Optionally, the interconnect 216 may include a cannulated passage 217 extending along a longitudinal axis of the interconnect 216 between both ends. At least one of the fixation elements 212, 214 includes a cannulated passage 221. The cannulated passage 221 extends from the proximal end 224 (e.g., from the cavity 228) to the distal end 226. In practice, a guide pin may be inserted into the end of the bone, for example, along the longitudinal axis of the bone. A pilot hole may optionally be formed over a portion of the guide pin, for example using a cannulated drill bit. One or more of the cannulated fixation elements (e.g., cannulated fixation element 240) may be advanced over the guide pin such that the guide pin is received within the cannulated passage 221 and the fixation elements 212, 214 may be secured into the bone as described herein. Optionally, a cannulated interconnect 216 may also be advanced over the guide pin.

Again, while only one fixation element 214 is illustrated with cannulated passage 221, it should be understood that both fixation elements 212, 214 may include a cannulated passage 221. One advantage of having only one cannulated fixation element 214 is that a guide pin may be inserted into the cavity 228 of the first fixation element 212 and may abut against the distal end 229. The distal end 229 may therefore prevent the guide pin from moving beyond the first fixation element 212 when the second bone is urged against the guide pin.

Alternatively (or in addition), a guide pin may be used which includes a flange extending radially outwardly having a diameter greater than the diameter of the cavity 228. The flange may be position a distance away from an end of the guide pin such that a portion of the guide pin is received within the cavity 228 of the first fixation element 212 when the flange abuts against the proximal end 224 of the first fixation element. The flange may therefore prevent the guide pin from advancing though the first fixation element 212, even if the first fixation element 212 is cannulated.

Figure 11C:
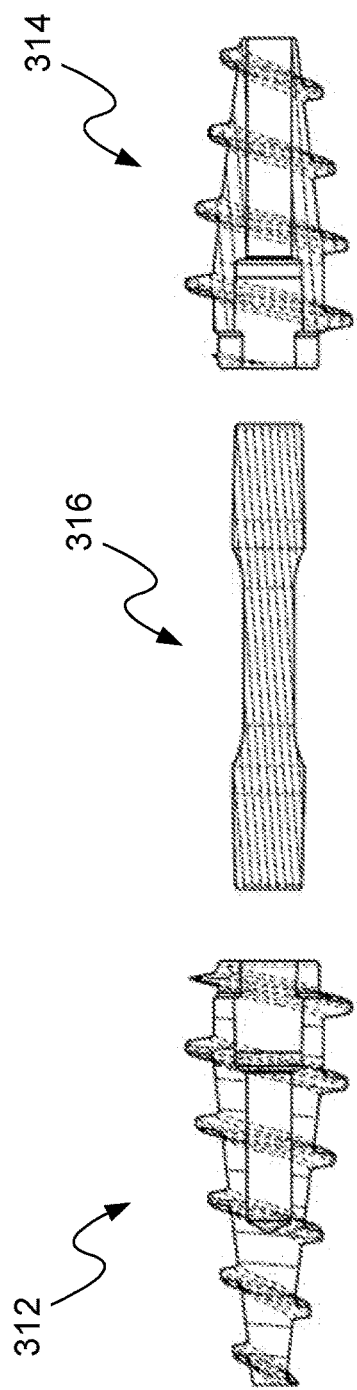
Figure 11D:
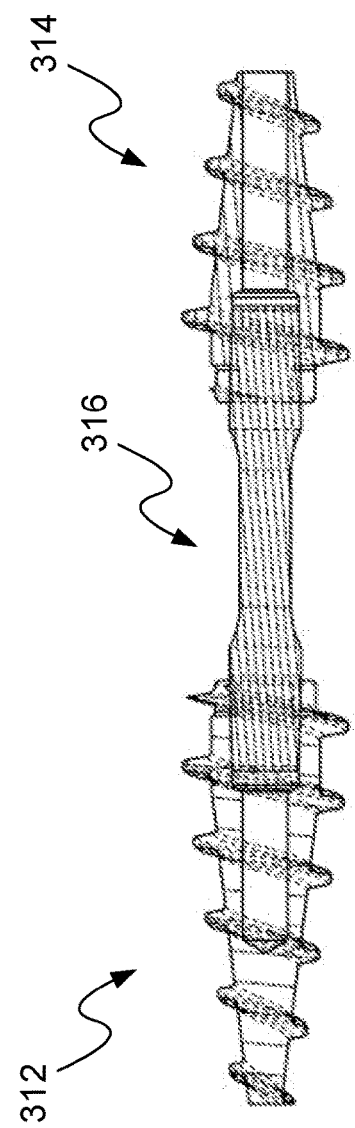

Turning now to FIGS. 11a-11d, various view of another embodiment of a fixation system 300 are generally illustrated. In particular, FIG. 11a is an exploded view, FIG. 11b is an assembled view, FIG. 11c is an exploded cross-sectional view, and FIG. 11d is a cross-sectional assembled view of the fixation system 300. The fixation system 300 includes a first and a second fixation element 312, 314 as well as an interconnect 316. The first and second fixation elements 312, 314 are similar to any of the fixation elements described herein. The interconnect 316 may include tapered surfaces 338, 340 which are separated by a flexible region 369. The tapered surfaces 338, 340 are configured to engage with the cavities 328 of the first and second fixation elements 312, 314 as described herein. The flexible region 369 is configured to allow the first and second fixation elements to move (e.g., bend) with respect to each other such that the two bones secured together by the fixation system 300 (when assembled) can move. For example, at least a portion of the interconnect 316 (e.g., at least the flexible region 369) may include a superelasticity and/or shape memory material such as, but not limited to, nickel titanium alloys nitinol (e.g., an alloy of nickel and titanium).

The dimensions of the flexible region 369 may be selected to allow the bending characteristics of the interconnected 316 to be adjusted. For example, the cross-sectional dimensions, shape, and/or length of the flexible region 369 may be adjusted to increase the range of motion (e.g., bending) of the fixation system 300, the amount of force necessary to bend the fixation system 300, and/or the direction(s) in which the fixation system may bend. For example, FIGS. 12a-12d generally illustrates one embodiment of a fixation system 400 including a first and a second fixation element 412, 414 and an interconnect 416 having a flexible region 469 configured to allow the fixation system 400 to bend in a generally only one direction (e.g., generally only in a single plane). For example, at least a portion of the flexible region 469 may have a generally rectangular cross-section having a length running along the longitudinal axis of the interconnect 416 and a width and height generally perpendicular thereto. The dimensions of the width or the height may be selected to provide directional movement and stability of the interconnect 416 such that the interconnect 416 will generally only bend in one direct as a result of the forces in which the fixation system 400 will experience in a normal or typical application (e.g., the forces that the fixation system 400 would likely experience when installed in a foot, hand, or the like).

While the fixation system 400 is illustrated having a generally rectangular cross-section, this is not a limitation of the present disclosure unless specifically claimed as such. For example, at least a portion of the flexible region 469 may have a generally oval cross-section, one or more longitudinal and/or transverse ribs, grooves, or the like.

A benefit of the fixation systems 300, 400 is that they may allow for some degree of flexibility when used to couple to adjacent bones which originally were coupled together by way of a joint. In the fixation systems 300, 400, the interconnects 316, 416 may have a separation length (i.e., distance between the first and second fixation elements when assembled) which is greater than the separation length of the other embodiments described herein. The larger separation length may facilitate bending of the fixation systems when assembled. The fixation systems may have a diameter of approximately 0.5 to 4 mm, an overall length of between approximately 5 to 20 mm, and may bend up to an angle between 10 degrees to 60 degrees.

Figure 13:
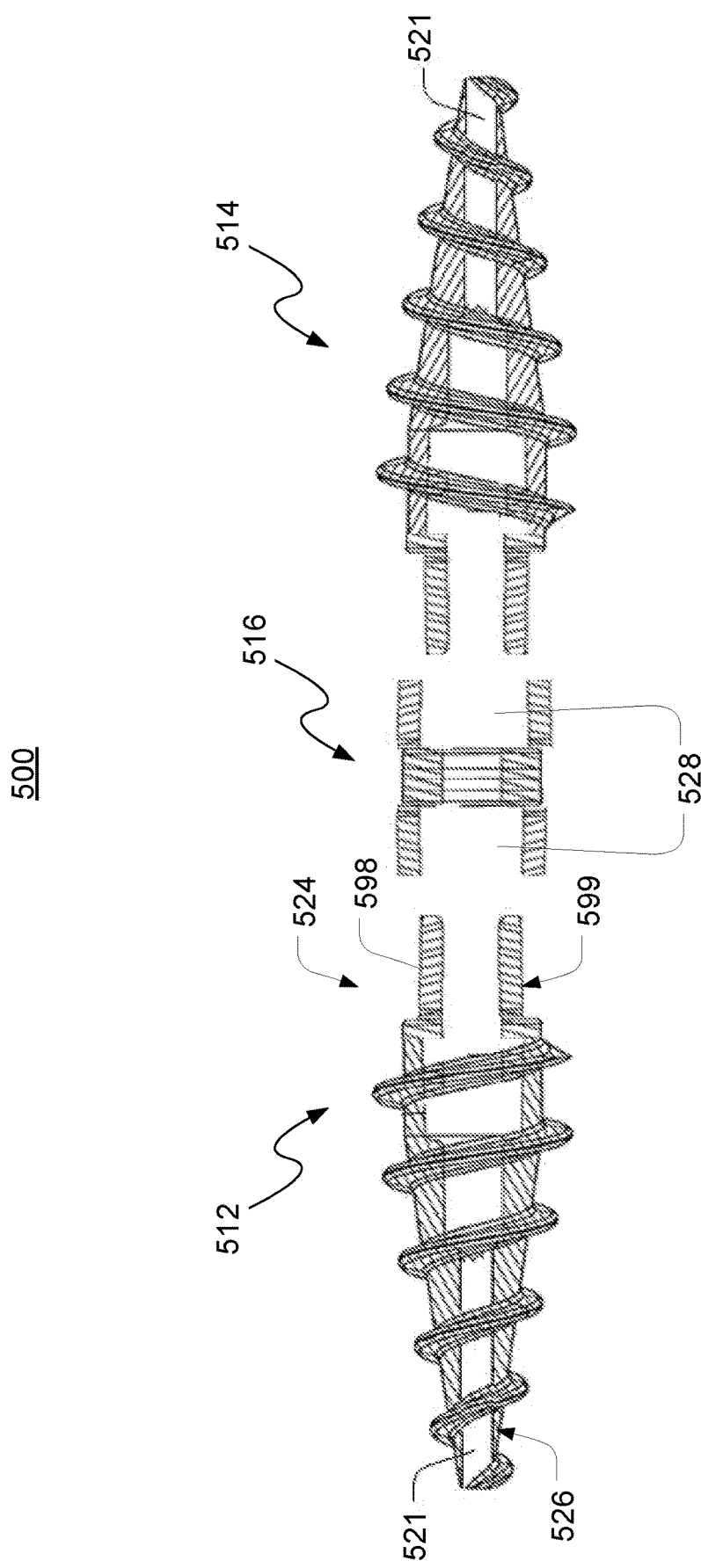
FIG. 13 is a cross-sectional exploded view of another fixation system consistent with the present disclosure.

Turning now to FIG. 13, yet another embodiment of a fixation system 500 consistent with the present disclosure is generally illustrated. The fixation system 500 includes a first and a second fixation element 512, 514 and an interconnect 516. At least one of the fixation elements 512, 514 includes a generally cylindrical protrusion 598 extending outwardly from the proximal end 524. The generally cylindrical protrusion 598 has a tapered external surface 599. The interconnect 516 includes at least one tapered generally cylindrical cavity 528 having a tapered internal surface 530 configured to frictional engage the corresponding tapered external surfaces 599 of protrusions 599 of the corresponding fixation elements 512, 514. While the fixation system 500 is illustrated in which interconnect 516 includes a first and a second tapered generally cylindrical cavity 528 and the interconnect includes a first and a second tapered generally cylindrical protrusion 598, it should be understood that either of the fixation elements 512, 514 may include a tapered cavity as described herein and the corresponding end of the interconnect 516 may have a tapered protrusion as described herein.

Figure 14:
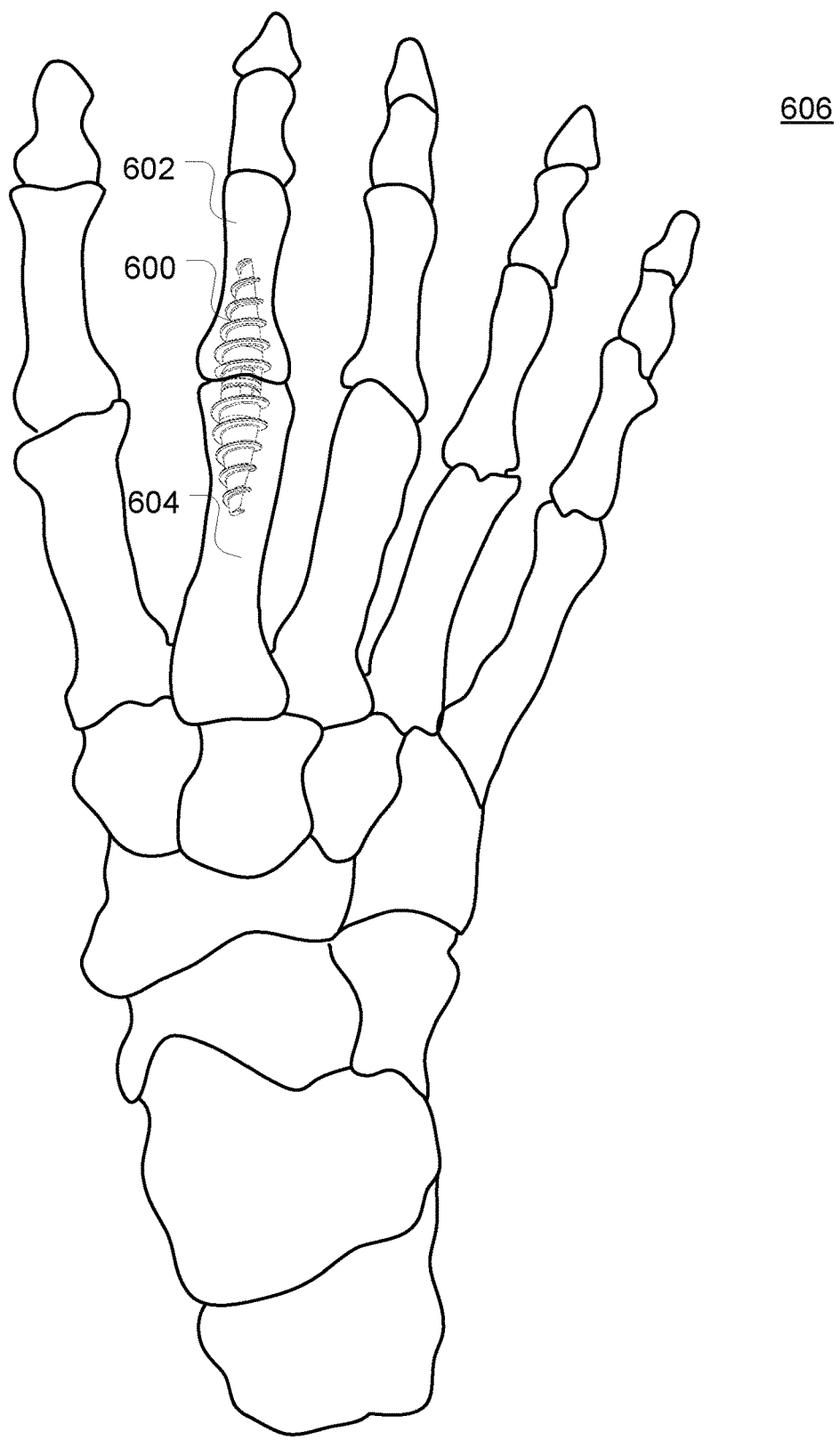
FIG. 14 generally illustrates one embodiment of a fixation system securing two bones in a foot consistent with one embodiment of the present disclosure.
Figure 15:
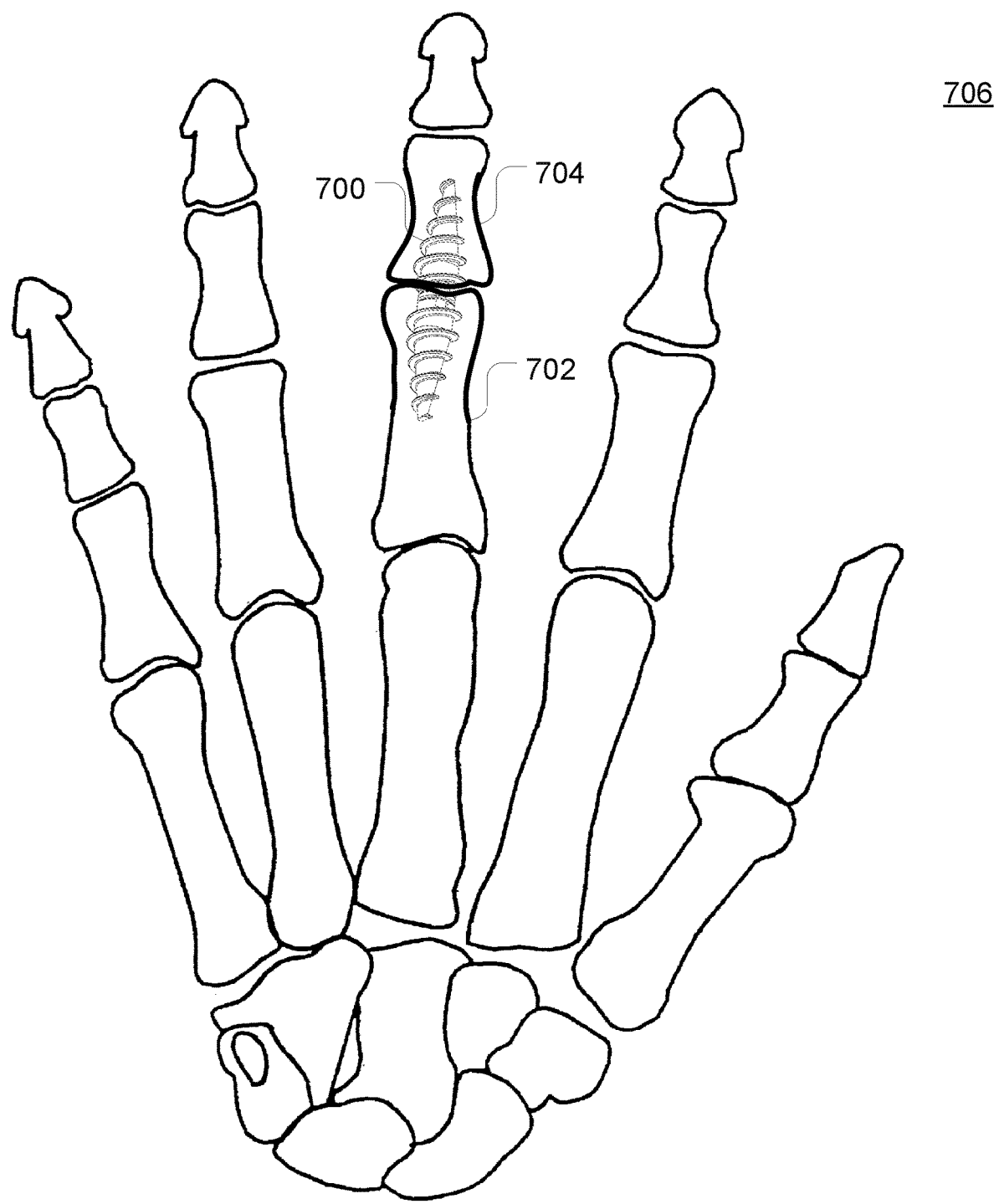
FIG. 15 generally illustrates one embodiment of a fixation system securing two bones in a hand consistent with one embodiment of the present disclosure.

The fixations systems described herein may be used to couple any two bones. For example, a fixation system 600 consistent herewith may be used to couple two or more bones 602, 604 in a foot 606 as generally illustrated in FIG. 14. A fixation system 700 consistent herewith may also be used to couple to or more bones 702, 704 in a hand 706 as generally illustrated in FIG. 15. It should be understood, however, that these are merely illustrative examples and that the fixation systems described herein are not limited to feet 606 and/or hands 706 unless specifically claimed as such.

It should be appreciated that various features of the different embodiments described herein may be combined together. For example, the interconnect may be eliminated such that that the two fixation elements may be directly coupled to each other, for example, using a tapered interference connection as described herein.

According to one aspect, the present disclosure features a fixation system for coupling a first and a second portion of bone together. The fixation system includes a first fixation element, a second fixation element, and an interconnect. The first fixation element includes an external surface configured to engage the first portion of bone and a first tapered mating surface. The second fixation element includes an external surface configured to engage the second portion of bone and a second tapered mating surface. The interconnect includes a first and a second tapered surface disposed at generally opposite ends. The first and the second tapered surfaces are configured to frictionally engage the first and the second tapered mating surfaces of the first and the second element, respectively, to form frictional interference connections therebetween.

According to another aspect, the present disclosure features a fixation system for coupling a first and a second portion of bone together including a first fixation element, a second fixation element, and an interconnect. The first fixation element includes a first body having an external surface configured to engage the first portion of bone. The first body defines a first generally cylindrical protrusion having a tapered external surface. The second fixation element includes a second body having an external surface configured to engage the second portion of bone. The second body defines a second generally cylindrical protrusion having a tapered external surface. The interconnect includes a first and a second tapered generally cylindrical cavity having a tapered internal surface configured to frictionally engage the tapered external surfaces of the first and the second protrusions.

According to yet another aspect, the present disclosure features a fixation system for coupling a first and a second portion of bone together including a first fixation element, a second fixation element, and an interconnect. The first fixation element includes a first body having an external surface configured to engage the first portion of bone. The first body defines a first generally cylindrical cavity having a tapered internal surface. The second fixation element includes a second body having an external surface configured to engage the second portion of bone. The second body defines a second generally cylindrical cavity having a tapered internal surface. The interconnect includes a first and a second tapered generally cylindrical protrusion having a tapered external surface configured to frictionally engage the tapered internal surfaces of the first and the second cavities.

While the principles of the present disclosure have been described herein, it is to be understood by those skilled in the art that this description is made only by way of example and not as a limitation as to the scope of the invention. The features and aspects described with reference to particular embodiments disclosed herein are susceptible to combination and/or application with various other embodiments described herein. Such combinations and/or applications of such described features and aspects to such other embodiments are contemplated herein. Other embodiments are contemplated within the scope of the present invention in addition to the exemplary embodiments shown and described herein. Modifications and substitutions by one of ordinary skill in the art are considered to be within the scope of the present invention, which is not to be limited except by the following claims.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

All references, patents and patent applications and publications that are cited or referred to in this application are incorporated in their entirety herein by reference.

While the principles of the present disclosure have been described herein, it is to be understood by those skilled in the art that this description is made only by way of example and not as a limitation as to the scope of the invention. The features and aspects described with reference to particular embodiments disclosed herein are susceptible to combination and/or application with various other embodiments described herein. Such combinations and/or applications of such described features and aspects to such other embodiments are contemplated herein. Other embodiments are contemplated within the scope of the present invention in addition to the exemplary embodiments shown and described herein. Modifications and substitutions by one of ordinary skill in the art are considered to be within the scope of the present invention, which is not to be limited except by the following claims.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents. Various features, aspects, and embodiments have been described herein. The features, aspects, and embodiments are susceptible to combination with one another as well as to variation and modification, as will be understood by those having skill in the art. The present disclosure should, therefore, be considered to encompass such combinations, variations, and modifications.

What is claimed is:

1. A fixation system for coupling together a first bone and a second bone, said fixation system comprising:
   (a) a first fixation screw comprising:
      (i) a first tapered external surface extending from a first wide end to a first narrow end, wherein the first tapered external surface is configured to at least partially engage with the first bone;
      (ii) a first cavity at least partially disposed in the first wide end comprising a first tapered mating recess; and
      (iii) one or more first notches disposed through at least a portion of the first tapered external surface and extending from the first wide end;
   (b) a second fixation screw comprising:
      (i) a second tapered external surface extending from a second wide end to a second narrow end, wherein the second tapered external surface is configured to at least partially engage with the second bone;
      (ii) a second cavity at least partially disposed in the second wide end comprising a second tapered mating recess; and
      (iii) one or more second notches disposed through at least a portion of the second tapered external surface and extending from the second wide end; and
   (c) an interconnect comprising:
      (i) a first tapered surface configured to frictionally engage with the first fixation screw within the first tapered mating recess to form a first frictional fit connection therebetween; and
      (ii) a second tapered surface extending in a substantially opposite direction from the first tapered surface of the interconnect, wherein the second tapered surface of the interconnect is configured to frictionally engage with the second fixation screw within the second tapered mating recess to form a second frictional fit connection therebetween;
   wherein the interconnect further comprises a flexible region disposed between the first tapered surface and the second tapered surface, such that the first fixation screw and the second fixation screw are able to move, bend, or both move and bend with respect to each other; and
   wherein the flexible region comprises at least one of a rib, and a groove, extending along a length of the flexible region.

2. The fixation system of claim 1, wherein at least one of the first notches and the second notches comprises a plurality of notches.

3. The fixation system of claim 1, wherein the first fixation screw, the second fixation screw, or both, are configured to engage with a driver to rotate at least one of the respective first fixation screw and second fixation screw.

4. The fixation system of claim 3, wherein the flexible region has a cross-sectional dimension configured to provide a range of flexibility based on an original anatomical joint of a patient.

5. The fixation system of claim 4, wherein the range of flexibility is between 0 degrees to 60 degrees, inclusive of 0 degrees and 60 degrees and all angles in between.

6. The fixation system of claim 3, wherein the flexible region has a generally rectangular cross-sectional shape, wherein a short axis of the rectangular cross-sectional shape is dimensioned to provide flexibility in a plane defined by the short axis.

7. The fixation system of claim 6, wherein a long axis of the generally rectangular cross-sectional shape is dimensioned to limit flexibility in a plane defined by the long axis.

8. The fixation system of claim 1, wherein at least a portion of the flexible region comprises a superelastic material, a shape memory material or both the superelastic material and the shape memory material.

9. The fixation system of claim 1, wherein the flexible region comprises a shoulder extending radially outwards from at least a portion of a body of the interconnect.

10. The fixation system of claim 9, wherein the shoulder extends circumferentially about a circumference of the body of the interconnect.

11. The fixation system of claim 9, wherein the shoulder is configured to limit the distance which the first tapered surface and the second tapered surface are inserted within the respective first tapered mating recess and the second tapered mating recess.

12. The fixation system of claim 1, wherein at least one of the first fixation screw and the second fixation screw comprises a self-tapping thread extending outwardly from the respective first tapered external surface and second tapered external surface.

13. The fixation system of claim 1, wherein at least one of the first notches and the second notches is configured to engage with a driver to rotate the screw into the bone.

14. The fixation system of claim 1, wherein the interconnect, the first fixation screw and the second fixation screw, when coupled together, have an overall length of approximately 5 mm to 20 mm, inclusive, and an overall diameter of approximately 0.5 mm to 4 mm, inclusive.

15. The fixation system of claim 1, wherein a length of the first fixation screw is approximately equal to a length of the second fixation screw.

16. The fixation system of claim 1, wherein the first fixation screw further comprises a cannulated passage extending from the wide end through the narrow end of the first fixation screw.

17. The fixation system of claim 1, wherein the interconnect has a length dimension that is selected such that, when the first and second fixation screws are installed into the first and second bones, respectively, and coupled together via the interconnect, a distance between the first and second bones is about an original anatomical distance between the first and second bones.

* * * * *